United States Patent

Thanoo et al.

[11] Patent Number: 5,945,126
[45] Date of Patent: Aug. 31, 1999

[54] CONTINUOUS MICROSPHERE PROCESS

[75] Inventors: Bagavathikanun Chithambara Thanoo, Broadview Heights; James Murtagh, Hudson, both of Ohio

[73] Assignee: Oakwood Laboratories L.L.C., Oakwood, Ohio

[21] Appl. No.: 08/800,924

[22] Filed: Feb. 13, 1997

[51] Int. Cl.⁶ .................................................. A61K 9/14
[52] U.S. Cl. ................ 424/489; 424/486; 424/497; 424/425
[58] Field of Search ........................... 424/497, 489, 424/486, 425

[56] References Cited

U.S. PATENT DOCUMENTS

| | | |
|---|---|---|
| 3,645,911 | 2/1972 | Van Besauw et al. . |
| 3,755,558 | 8/1973 | Scribner . |
| 3,773,919 | 11/1973 | Boswell et al. . |
| 3,891,570 | 6/1975 | Fukushima et al. . |
| 4,384,975 | 5/1983 | Fong . |
| 4,389,330 | 6/1983 | Tice et al. . |
| 4,652,443 | 3/1987 | Yoshida et al. . |
| 4,668,580 | 5/1987 | Dahm et al. . |
| 4,692,188 | 9/1987 | Ober et al. . |
| 4,767,628 | 8/1988 | Hutchinson . |
| 4,818,542 | 4/1989 | Deluca et al. . |
| 4,898,696 | 2/1990 | Sliwka . |
| 4,954,298 | 9/1990 | Yamamoto et al. . |
| 5,049,322 | 9/1991 | Devissaguet et al. . |
| 5,118,528 | 6/1992 | Fessi et al. . |
| 5,183,690 | 2/1993 | Carr et al. . |
| 5,304,377 | 4/1994 | Yamada et al. . |
| 5,330,767 | 7/1994 | Yamamoto et al. . |
| 5,389,379 | 2/1995 | Dirix et al. . |
| 5,407,609 | 4/1995 | Tice et al. . |
| 5,476,663 | 12/1995 | Okada et al. . |
| 5,480,868 | 1/1996 | Kamei et al. . |
| 5,534,269 | 7/1996 | Igari et al. . |
| 5,585,460 | 12/1996 | Yamada et al. . |
| 5,611,971 | 3/1997 | Maedera et al. . |
| 5,631,020 | 5/1997 | Okada et al. . |
| 5,631,021 | 5/1997 | Okada et al. . |
| 5,718,921 | 2/1998 | Mathiowitz et al. .................... 424/497 |

FOREIGN PATENT DOCUMENTS

| | | |
|---|---|---|
| 0274961 | 7/1988 | European Pat. Off. . |
| 2237206 | 7/1971 | Germany . |
| 1405108 | 9/1975 | United Kingdom . |
| WO95/13799 | 5/1995 | WIPO . |

OTHER PUBLICATIONS

Ross Introduces New Sollid–Liquid Injection Manifold (SLIM™) for Instant Addition of Ingredients sell sheet by Charles Ross & Son Company, Apr. 1995.

R. Jeyanthi et al., Effect of solvent removal technique . . . , Journal of Controlled Release 38 (1996) 235–244.

P.J. Burns et al., Evaluation of a new continuous process for preparation of progesterone . . . p. 7603 (1991).

Primary Examiner—Thurman K. Page
Assistant Examiner—William E. Benston, Jr.
Attorney, Agent, or Firm—Watts Hoffman Fisher & Heinke

[57] ABSTRACT

A continuous process for producing microspheres wherein small particle sizes can be obtained without the problem of foaming. A drug and polymer containing dispersed phase is continuously introduced into a high intensity emulsification vessel along with a continuous phase. An emulsion of the dispersed phase is formed in the continuous phase by high intensity mixing effective to quickly solidify the dispersed phase polymer without having to take steps to address foaming.

26 Claims, 1 Drawing Sheet

CONTINUOUS MICROSPHERE PROCESS

BACKGROUND OF THE INVENTION

Microcapsules and Microspheres formed from various natural and synthetic polymers and resins have become popular delivery vehicles for various active agents such as drugs, diagnostic reagents and the like. Degradable microcapsules and microspheres are of particular interest for use in so called "depot" formulations, where delivery of the active agent over an extended period of time is desired. Despite the growing number of uses of microcapsules and microspheres, there remains a need for an economic and reliable method for their manufacture that avoids the most significant wastes and expenses associated with existing methods, while simultaneously providing products having the most desirable properties.

Processes for preparing microspheres typically involve the formation of at least one dispersed phase in a continuous phase. The dispersed phase typically includes the active agent and polymer and, upon solidification in the continuous phase, becomes a microsphere. Microcapsules are similarly formed using multiple phases. In a typical practice, a water-oil-water (w/o/w) emulsion is formed, and the polymer caused to precipitate out of one phase onto the surface of a dispersed phase to form a capsule wall thereon upon solidification of the polymer.

One difficulty with current processes is their inability to efficiently produce small particles that exhibit all of the desired properties of drug incorporation, low residual solvent and scalability. When microspheres are intended for subcutaneous, intramuscular or intravenous delivery, small particles are required. However, obtaining small particles typically requires a continuous phase having a high surfactant concentration and/or viscosity of the continuous phase, and/or a low viscosity dispersed phase. This can necessitate adjusting the viscosity and increases the energy input needed for small particles, thereby further complicating the process. Moreover, it is often necessary to use a highly viscous dispersed phase in order to obtain higher drug loads. However, it is extremely difficult to obtain small particles with a highly viscous dispersed phase. Moreover, the stirring required to obtain the desired particle sizes frequently results in excessive foaming, especially when increased surfactant concentrations or lower viscosity continuous phases are used. This is problematic in many systems because, while cooling the system will increase the viscosity and help to stabilize the droplets and reduce foaming, the viscosity of the DP will tend to increase more dramatically than, for example, a typically aqueous continuous phase. This will make it more difficult to obtain small droplets. Still further, if the concentration of the drug is close to the solubility limit of the dispersed phase solution, the drug could crystalize out of the system, which can result in low drug incorporation and burst problems in the release profile.

In many cases, foaming will make it impossible to obtain the desired particle size. In other cases, the dispersed phase droplets will escape the mixing zone and will result in larger particles and an unacceptable particle size distribution. In still other cases, a suitable particle size might be achieved, but drug load is inefficient, which can render the process commercially unviable.

Another problem encountered with existing processes occurs in scale up. Once one obtains a batch of microspheres or microcapsules having the desired characteristics, such as particle size, drug load, release profile and the like, it is then necessary to scale up the process for commercial production. Scaling up to commercial production typically involves several successively larger production runs, with various process parameters changing with each successive scale up. A great deal of experimentation can be necessary to finally obtain a commercial scale batch having the characteristics of the initial run. When a single gram of some of today's more exotic drugs can cost many thousands of dollars, having to experiment at each successive level of scale up can be extremely expensive. Likewise, the time and capital expense associated with the scale up of such processes can put one at a significant competitive disadvantage.

There is a need for a process that can efficiently produce small particle sizes with good drug loading in a continuous manner. The process must be easily adapted to a wide variety of active agents and polymers, enable economic and efficient scale up to commercial production and produce uniform products throughout a given production run.

DISCLOSURE OF THE INVENTION

The present invention is directed to a continuous process for producing active agent containing polymer bodies, and more particularly microspheres. The microspheres produced according to the inventive process are ideal for carrying drugs, diagnostic reagents, or various other active agents. Not only is the inventive process continuous, it also provides a simple, economic and efficient means of scaling up from a test batch to full production while maintaining a product having uniform characteristics throughout the production cycle. No successively larger batches are required to scale up. Once a desired formulation is achieved on a small scale, one need only run the process for a longer period of time in order to obtain any desired batch size. Advantageously, the microspheres produced throughout the process have excellent uniformity.

Moreover, foaming can be minimized or entirely eliminated in the practice of the inventive process, without having to increase the viscosity of the continuous phase. Small particle sizes having high drug loads and low residual solvent concentrations are easily obtained in the inventive process, even when it is necessary to employ a viscous dispersed phase. It is extremely difficult, if not impossible, to obtain useful small particles with a highly viscous dispersed phase using current processes. The inventive process advantageously provides a great deal of flexibility in adjusting various parameters such as size, without jeopardizing loading efficiency, yield or uniformity, which enables use of the microspheres of the invention in a wide variety of delivery methods. For example, one advantage of the preferred embodiment is that mixing intensity can be adjusted independently of the flow rates of either or both of the dispersed and continuous phases, which provides significant flexibility.

Accordingly, it is an aspect of the invention to provide a continuous method of making active agent containing polymer bodies comprising forming a dispersed phase comprising active agent and polymer; providing a continuous phase in which said dispersed phase will form an emulsion; continuously introducing dispersed phase into a reactor vessel at a dispersed phase feed rate, and continuous phase into said reactor vessel at a continuous phase feed rate, said reactor vessel including means for forming an emulsion, and forming an emulsion of said dispersed phase in said continuous phase; and finally, continuously transporting said emulsion from said reactor vessel to a solvent removal vessel to remove solvent.

In one aspect of the invention the dispersed phase is fed to said reaction vessel at a rate of from about 4 ml/min to about 400 ml/min, and said continuous phase is fed to said reactor vessel at a rate of from about 1000 ml/min. to about 20,000 ml/min. In a preferred embodiment, the dispersed phase includes a hydrophilic peptide active agent and a copolymer of lactide and glycolide, and the process comprises emulsifying the dispersed and continuous phases in a manner effective to provide an average particle size of from about 5 µm to about 40 µm, and an active agent load of at least about 9%. Still more preferably, the average particle size of from about 5 µm to about 40 µm, and the active agent load is at least about 15%.

In one embodiment the continuous phase and dispersed phase are introduced into the reactor in a ratio of from 5:1 to 500:1. More preferably, the continuous phase and dispersed phase are introduced into the reactor in a ratio of from 40:1 to 200:1 and, more preferably still about 80:1. Preferably, the method comprises emulsifying said dispersed and continuous phases in a manner adapted to cause solidification of said dispersed phase polymer within about 10 seconds. Still more preferably solidification occurs within about 5 seconds. In one aspect of the invention, the means for forming an emulsion produces a mixing zone effective to cause solidification of dispersed phase polymer within about 10 seconds, and said dispersed phase is introduced into said reaction vessel in said mixing zone.

In a preferred aspect of the method the means for forming an emulsion comprises an impeller. In one embodiment, the method comprises forming said emulsion by running said impeller in excess of about 5,000 revolutions per minute. In another embodiment, the impeller is run at from about 6,000 to about 10,000 revolutions per minute. It is another aspect of the invention that the diameter of said impeller define a diameter of a cylindrical zone extending axially from said impeller, and said dispersed phase is introduced into said axially extending zone.

In one embodiment the dispersed phase is a homogeneous solution. In another embodiment the dispersed phase is an emulsion. In a preferred embodiment the average residence time of said dispersed phase in said reactor is less than about 5 seconds.

It is another aspect of the invention that the method steps are carried out for a period sufficient to produce a desired population of microspheres, and wherein the microspheres produced at the beginning of said period have substantially the same size and agent load as microspheres produced at the end of said period.

It is yet another aspect of the invention to provide a method of scaling up the production of active agent containing polymer bodies from a first population having a desired average particle size and agent loading, to a second, larger population having substantially the same average particle size and agent loading. This embodiment comprises introducing a continuous phase and a dispersed phase containing said active agent and polymer into a reactor vessel, and mixing said phases to form an emulsion of said dispersed phase in said continuous phase in said vessel; continuously transferring the emulsion from said reactor vessel to a solvent removal vessel and removing solvent from said emulsion therein; obtaining said first population having said desired average particle size and agent loading; and, thereafter, selecting a suitable duration for continuously performing the first two steps to produce a desired second larger population of agent containing polymer bodies, and continuously performing the first two steps for a period sufficient to obtain said second population.

In a preferred aspect of this embodiment the desired average particle size and agent loading in said first population is obtained by performing the first two steps, and adjusting at least one parameter selected from the feed rate of said dispersed phase into said reactor vessel, the feed rate of said continuous phase into said reactor vessel, and the intensity by which said continuous and dispersed phases are mixed, to obtain said desired average particle size and agent loading.

It is yet another aspect of the invention to provide microspheres made by the method disclosed herein.

Many additional features, advantages and a fuller understanding of the invention will be had from the following detailed description of the preferred embodiments and accompanying drawing.

DETAILED DESCRIPTION OF THE PREFERRED EMBODIMENTS

Figure 1:
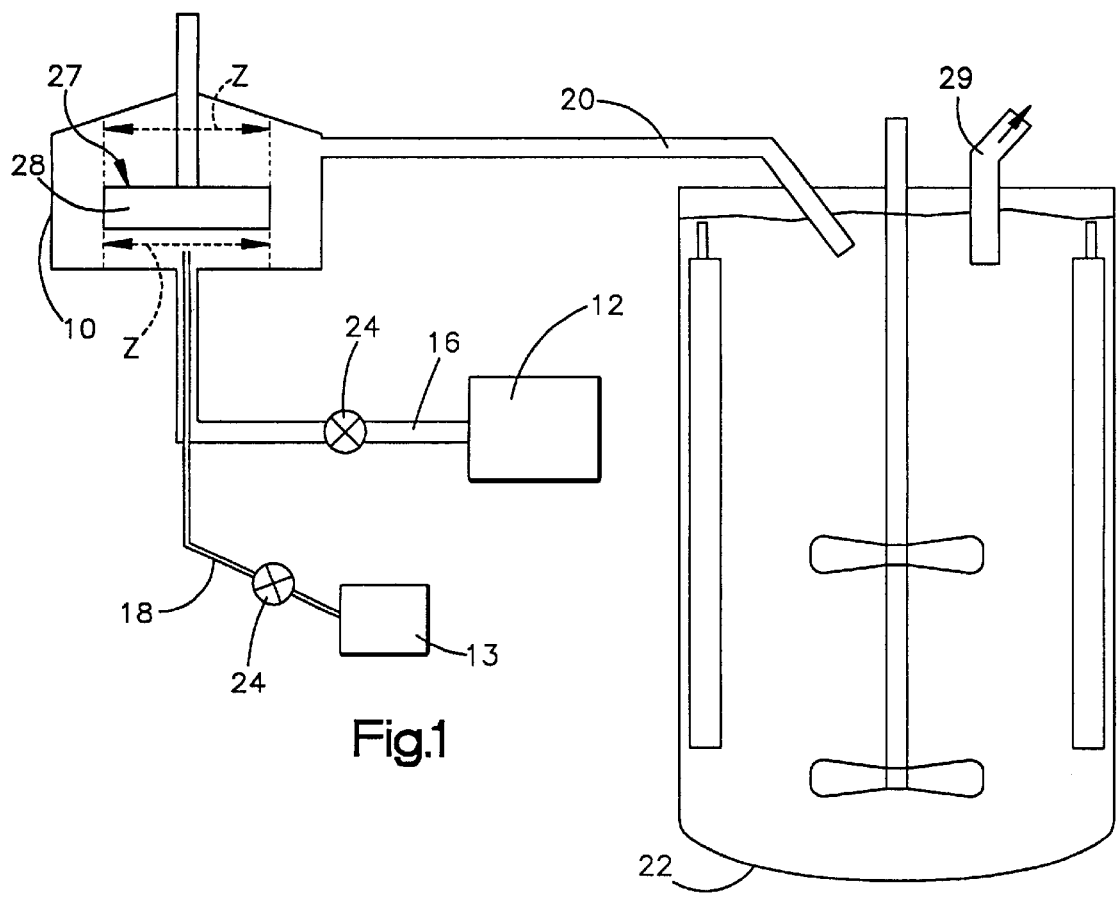
FIG. 1 is a stylized schematic representation of an apparatus useful in carrying out the process of the invention.

In the preferred process of the invention a dispersed phase includes a polymer and an active agent. It will be apparent to those of ordinary skill in the art in view of the present disclosure that the active agent can be any agent for which encapsulation or interspersion within a small polymer body is desired. Preferably, the active agent is a drug or diagnostic agent and the microspheres are intended for the delivery of such drug or diagnostic agent to a patient in need thereof. The preferred drugs may be peptide drugs, proteinaceous drugs, steroidal drugs, non-steroidal drugs, simple compounds and so on. A representative list of suitable drugs and other active agents may be found in U.S. Pat. Nos. 5,407,609, 4,767,628, 3,773,919 and 3,755,558, all incorporated herein by reference. Of particular interest are LH-RH agonists such as leuprolide, triptorelin, goserelin, nafarelin, historelin and buserelin, LH-RH antagonists, somatostatin analogs such as octreotide, human, salmon and eel calcitonin, growth hormones, growth hormone releasing hormones, growth hormone releasing peptide, parathyroid hormones and related peptides, interferon, erythropoietin, GM-CSF, G-CSF, thymosin, antitrypsin, enterostatin, and chemotherapy drugs, antibiotics and analgesics for regional administration. An especially preferred drug for use in the instant invention is leuprolide.

In order to incorporate the active agent into the dispersed phase it is usually necessary to dissolve the active agent in a solvent. Solvents for the active agent will of course vary depending upon the nature of the agent. Typical solvents that may be used in the dispersed phase to dissolve the active agent include water, methanol, ethanol, dimethyl sulfoxide (DMSO), dimethyl formamide, dimethyl acetamide, dioxane, tetrahydrofuran (THF), methylene chloride, ethylene chloride, carbon tetrachloride, chloroform, lower alkyl ethers such diethyl ether and methyl ethyl ether, hexane, cyclohexane, benzene, acetone, ethyl acetate, and the like. Selection of suitable solvents for a given system will be within the skill in the art in view of the instant disclosure.

Polymers useful in the present invention can also vary. Examples of polymers known to those of ordinary skill in the art, and useful in the present invention, may be found in, for example, U.S. Pat. Nos. 4,818,542, 4,767,628, 3,773,919, 3,755,558 and 5,407,609, incorporated herein by reference. In selecting a particularly desirable polymer for a given system, numerous factors can be considered for purposes of producing a product having the desired clinical characteristics such as biodegradability (e.g., release profile) and biocompatibility. Once one of ordinary skill in the art has selected a group of polymers that will provide the desired clinical characteristics, then the polymers can be evaluated for desirable characteristics that will optimize the manufacturing process. For example, in some instances, it may be possible to select a polymer that will interact with the active agent in a manner that will facilitate the processing of the microspheres, enhance drug load, enhance solvent removal from the dispersed phase or inhibit drug migration from the dispersed phase into the continuous phase.

One consideration in selecting a preferred polymer is the hydrophilicity/hydrophobicity of the polymer. Both polymers and active agents may be hydrophobic or hydrophilic. Where possible it is desirable to select a hydrophilic polymer for use with a hydrophilic active agent, and a hydrophobic polymer for use with a hydrophobic active agent. In the preferred LH-RH microspheres, an ionic interaction between the drug and the hydrophilic carboxyl groups of the polymer is believed to enhance the drug load. In general, however, since hydrophilic drugs are soluble in water, if there is no affinity between the polymer and drug, or solidification is not sufficiently fast, drug load may decrease. It is also possible to use a hydrophilic drug in a hydrophobic polymer.

In selecting a particular polymer, the effect of the hydrophobicity/hydrophilicity of the polymer on the residual solvent in the system should also be considered. A hydrophilic polymer can be expected to yield low residual solvent with a hydrophilic drug, such as a hydrophilic peptide. In the case of the preferred leuprolide microspheres, the drug has a tendency to help eliminate hydrophobic solvent from the dispersed phase droplets quickly and efficiently. In addition, it has been observed that a greater drug load tends to correlate to lower residual solvent concentrations. Thus, in some systems, there is an indirect benefit with lower residual solvent when incorporating hydrophilic drugs in hydrophilic polymers. However, since there are other influencing factors on residual solvent other than hydrophilicity, this effect may not uniformly apply to non-peptide drugs. Nevertheless, it should follow that active agents that enhance the elimination of solvent from the dispersed phase droplet, without concomitant drug loss, yield superior products.

Another consideration is molecular weight of the polymer. While the molecular weight of the polymers will obviously impact on the product characteristics such as release rate, release profile and the like, it can also impact the process of producing the microspheres. Higher molecular weight polymers are typically associated with a more viscous dispersed phase, resulting in larger particles or increased difficulties in obtaining small particles and, in some instances, increased residual solvent. By contrast, lower molecular weight polymers are typically associated with slower solidification because the polymer tends to be more soluble. In the preferred system, higher residual solvent, higher drug loading and enhanced incorporation efficiency has been found to result from the use of higher molecular weight polymers. One advantage of the inventive process is its ability to form good, small, low residual solvent microspheres with high molecular weight polymers and, hence, viscous dispersed phases. Of course, the particular selection will also depend upon the desired product characteristics. For example, the higher the molecular weight, the longer the degradation time in the body and the longer the duration of drug release.

Still further, the particular polymer concentration employed can effect the system, not only from a product morphology standpoint, but also from a processing standpoint. An increase in polymer concentration tends to be associated with a higher drug load because a viscous dispersed phase needs to eliminate less solvent for solidification. An increased solidification rate tends to cause higher drug retention. Moreover, a viscous dispersed phase leads to less drug diffusion into the continuous phase during solidification. In some systems this may also result in higher residual solvent. In the preferred embodiments, polymer concentration in the dispersed phase will be from about 5 to about 40%, and still more preferably from about 8 to about 30%.

Especially preferred polymers are homopolymers of lactic acid, or copolymers of lactic acid and glycolic acid, i.e., poly(lactide-co-glycolide) or "PLGA" polymers. The ratio of lactic acid residues to glycolic acid residues can vary, and will typically range from 25:75 to 75:25, although even a 10% glycolide could find use since high lactide content results in lower viscosity and higher solubility. Preferred copolymers comprise at least about 50% lactic acid residues, such as 50:50 or 75:25 polymers. Poly(lactide-co-glycolide) copolymers are commercially available from a number of sources and can be readily prepared by conventional synthetic routes. Boeringer Ingleheim produces suitable polymers under the designations RG 502, RG 502H, RG 503, RG 503H, RG 752, RG 756 and others. With the preferred LH-RH microspheres RG502H and RG503H are used in the dispersed phase in concentrations of 23% and 13% respectively. Such copolymers also may be made by polymerizing lactic acid and glycolic acid or, preferably, by polymerizing the cyclic dimers of lactic acid and glycolic acid, namely lactide and glycolide, as described in, for example, U.S. Pat. No. 3,773,919, incorporated by reference above. Selection of a suitable polymer for a given system would be apparent to those of ordinary skill in the art in view of this disclosure.

Solvents for the polymer will also vary depending upon a number of factors, including the nature of the polymer, the active agent, toxicity, compatibility with other solvents in the system and even the use to which the microsphere will be put. Thus, in addition to dissolving the polymer, the solvent must be immiscible with the continuous phase in order to form droplets, highly volatile for optimum evaporation efficiency, and desirably non-flammable for safety reasons. Solvents suitable for the preferred poly(lactic) or poly(lactide-co-glycolide) polymers include methylene chloride, chloroform, ethyl acetate, substituted pyrrolidone and the like. In some instances, the solvent for the active agent will be the same as the solvent for the polymer. Some drugs, typically diagnostic agents such as radioactive inorganic salts used in imaging analysis, are not soluble or only slightly soluble in organic solvents. In these instances, a fine, sub-sub micron size powder can be directly suspended in the polymer solution to form microspheres. Although resort to this will be rare in drug delivery, it may prove useful with diagnostic agents. Selection of other solvents useful in accordance with the process of the invention will be within the skill in the art in view of the instant disclosure.

The polymer, active agent and solvent or solvents are combined to form the dispersed phase. In the preferred embodiment, the dispersed phase is a true, homogeneous solution which may be prepared by mixing the polymer, solvent and active agent together to form a solution. Alternatively, separate solutions of polymer and active agent can be prepared, each in its own solvent, and subsequently mixed to form the dispersed phase solution. In some instances, due to the nature of the active agent and/or polymer, the dispersed phase must be formed as an emulsion. For example, when a given proteinaceous drug is dissolved in a suitable active agent solvent, the resulting solution may be completely immiscible with a solution of the polymer in a particular polymer solvent. In order to provide a relatively homogeneous dispersed phase in which the drug and polymer are relatively uniformly interspersed, the drug and drug solvent may be emulsified with the polymer and polymer solvent to form a dispersed phase emulsion. Upon introduction of the dispersed phase into the continuous phase a w/o/w emulsion is formed. In still other systems, the dispersed phase can be prepared by forming a direct suspension of the active agent in a polymer solution.

In accordance with the inventive process described below, the dispersed phase heretofore described is dispersed or emulsified in a continuous phase in order to form droplets or inclusions of dispersed phase in the continuous phase. As used herein the terms emulsified or dispersed are intended in their broadest sense as meaning discrete regions of dispersed phase interspersed within the continuous phase. The noted inclusions will typically occur as generally spherical droplets, but may in some instances be irregular inclusions due to particular emulsification conditions. Any suitable medium in which the dispersed phase will form droplets or inclusions may be used as a continuous phase, with those that provide a maximum solvent sink for the dispersed phase solvent being especially desirable. Frequently, the continuous phase will also contain surfactant, stabilizers, salts or other additives that modify or effect the emulsification process. Typical surfactants include sodium dodecyl sulphate, dioctyl sodium sulfo succinate, span, polysorbate 80, tween 80, pluronics and the like. Particular stabilizers include talc, PVA and colloidal magnesium hydroxide. Viscosity boosters include polyacrylamide, carboxymethyl cellulose, hydroxymethyl cellulose, methyl cellulose and the like. Buffer salts can be used as drug stabilizers and even common salt can be used to help prevent migration of the active agent into the continuous phase. One problem associated with salt saturation of the continuous phase is that PVA and other stabilizers may have a tendency to precipitate as solids from the continuous phase. In such instances a particulate stabilizer might be used. Suitable salts, such as sodium chloride, sodium sulfate and the like, and other additives would be apparent to those of ordinary skill in the art in view of the instant disclosure.

In the preferred embodiment, the continuous phase is water. The aqueous continuous phase will typically include a stabilizer. A preferred stabilizer is polyvinyl alcohol (PVA) in an amount of from about 0.1% to about 5.0%. Still more preferably, PVA is present in an amount of about 0.35%. Other stabilizers suitable for use in the continuous phase would be apparent to those of ordinary skill in the art in view of the instant disclosure.

The selection of particular polymers, solvents and continuous phases will of course vary depending on the active agent and the desired product characteristics. Once the desired product characteristics, such as clinical application, release profile and the like are established, there may nevertheless be some latitude in selecting polymers, solvents and continuous phases to facilitate the production process.

For example, in slow solidifying systems, or systems where small particles are desired, a viscous continuous phase and a higher concentration of stabilizer may be necessary to obtain the desired microspheres. Likewise, if necessary, the dispersed phase can be made more viscous by cooling, increasing the molecular weight of the polymer or increasing the concentration of the polymer. Of course, adjusting the viscosity of the continuous phase further complicates the process, and use of a dispersed phase with a high viscosity makes it more difficult to obtain small particles. Still further, in addition to complicating both the process and apparatus, cooling the viscous phase will have a tendency to reduce the solubility of the dispersed phase solvent therein, which can lead to higher residual solvent contents and/or longer solvent removal periods. Drug crystallization might also be a problem with cooling. An advantage of the preferred embodiment of the invention is that, because foaming is not a significant impediment, it is not necessary to cool or otherwise adjust the viscosity of the phases in order to obtain small particle sizes. The present process enables one to obtain small particle sizes even when it is necessary to use a viscous dispersed phase, without having to adjust the viscosity of the continuous phase to prevent foaming. This simplifies the process and reduces costs.

In carrying out the process, once the dispersed and continuous phases are prepared, they are fed to a reaction vessel in which the dispersed phase is interspersed or emulsified to form droplets or inclusions in the continuous phase as described below.

Referring to FIG. 1, the process is commenced after the reaction vessel 10 is primed with a suitable starting volume of continuous phase from continuous phase reservoir 12. In the case of, for example, a 90 mL reactor vessel 10, the starting volume will be on the order of about 70 mL. Of course, the actual starting or priming volume will depend on the size and configuration of the reactor vessel, the location of the harvest line 20 and, in the case of a closed reactor vessel, the minimum amount of head space needed to control foaming. Those of ordinary skill in the art can empirically select the suitable priming volume for any given system.

The reactor vessel 10 may be open or closed, and is preferably closed. Fluids are advantageously moved through the closed system by the pumping action of the mixer. In addition, a closed reaction vessel also reduces the potential for foaming problems. A preferred vessel 10 is commercially available from Silverson Machines Inc., designated as in-line mixer assembly for L4R/L4RT. In order to implement the advantageous features of the inventive process, the noted apparatus was modified to add a second inlet port for the dispersed phase as described in more detail below. The inlet tube had a diameter of approximately ⅕ to ¹/₁₀th the diameter of the inlet tube that comes with the apparatus. The tube tip was positioned approximately ¼ inch below the stirrer head.

Once reactor 10 is primed, continuous phase is pumped or drawn into reactor 10 via continuous phase feed line 16, and dispersed phase is simultaneously pumped or drawn into reactor 10 via dispersed phase feed line 18 from dispersed phase reservoir 13. In the case of an open reactor the continuous phase emulsion is continuously pumped or drawn from reactor 10 via harvest line 20 into solvent evaporation tank 22. In the preferred closed reactor 10, formed or forming microspheres are pumped from vessel 10 for subsequent processing by the action of the mixer. On a small pilot scale the dispersed phase is stored in a small, for example, 125 mL addition funnel, which is pressurized to feed into the reactor vessel. Continuous phase is retained in a large reservoir, but in large scale production both phases (fluids) can be contained in standard stainless steel pressure tanks. Thereafter, a metering valve in the continuous phase addition line can control the flow of continuous phase from the pressurized tank. Alternatively, for smaller scale apparatus, continuous phase can be pumped into the reactor from an unpressurized vessel using a calibrated peristaltic pump. The flow rate of the dispersed phase from, for example a pressurized glass or stainless steel vessel, can be uniformly controlled using a pre-calibrated micrometer needle valve. For large scale production valveless metering pump-dispensers from a non-pressurized tank might be used.

Two important aspects of the process of the invention involve the introduction of the dispersed phase and continuous phase into vessel 10. First, the ratio of the dispersed phase to the continuous phase, which can effect solidification rate, active agent load, the efficiency of solvent removal from the dispersed phase, and porosity of the final product, is advantageously and easily controlled by controlling the flow rate of the dispersed and continuous phases into vessel 10 via feed lines 16 and 18. Second, the droplet size, solidification rate and efficiency of solvent removal are also effected by where the dispersed phase is introduced into reactor 10 relative to the emulsification device. Each of these aspects of the invention are discussed in more detail below.

First, as noted, the ratio of dispersed phase to continuous phase effects the rate of solidification, the drug load and, importantly, the amount of residual solvent in the microsphere. At a minimum there must be enough continuous phase relative to dispersed phase solvent to create a sink for the dispersed phase solvent. Thus, as a minimum, the amount of continuous phase must be greater than the solubility limit of the dispersed phase solvent in the continuous phase. The maximum ratio of dispersed phase to continuous phase will be limited by the physical size of the apparatus used, the desired amount of head space, the size of the evaporation tank and the like. The general rule is that by increasing the amount of continuous phase, one creates a greater sink for the dispersed phase solvent. In addition, increasing the amount of head space in conjunction with an air sweep or other means of replacing or removing air/vapor from above the surface of the continuous phase can also enhance the sink nature of the continuous phase. In practice, this will be preferably done in a solvent removal tank and not in the reactor.

In between the maximum and minimum desired amounts of continuous phase to dispersed phase, the present process provides a great deal of flexibility in controlling and adjusting the ratio while simultaneously allowing the process to be run in a continuous manner. Advantageously, in the continuous process of the invention the ratio of dispersed phase to continuous phase can be easily controlled by controlling the feed rate of each to the reactor vessel. This in turn is easily and accurately accomplished using commercially available flow regulators, such as turbine, paddle wheel, gear-type, positive displacement or magnetic flowmeters, or valveless metering pumps or similar apparatus apparent to those of ordinary skill in the art. A unique benefit of the instant invention is that the ratio of dispersed phase to continuous phase can be constantly maintained throughout the entire process, which enables the consistent production of uniform microspheres throughout the entire duration of a given production run.

The actual ratios of continuous phase to dispersed phase will depend upon the desired product, the polymer, the drug, the solvents, etc., and can be determined empirically by those of ordinary skill in the art. In the preferred embodiment, the ratio of continuous phase to dispersed phase will typically range from about 5:1 to about 500:1, and more preferably about 40:1 to about 200:1. In the preferred LH-RH system the optimal ratio is about 80:1. This translates into flow rates for the dispersed phase of from about 1000 mL/min. to about 5 mL/min., more preferably from about 40 mL/min. to about 12 mL/min, and still more preferably about 25 mL/min., with a continuous phase flow rate fixed at 2000 mL/min. If the continuous phase flow rate is increased, the dispersed phase flow rate will change accordingly. On a production scale the continuous phase flow rate may be as high as 20,000 mL/minute in order to reduce the processing time. In the preferred process of making LH-RH microspheres, the flow rate of continuous phase will be on the order of about 2000 ml/min. and the flow rate of dispersed phase will be on the order of about 25 ml/min.

As shown in FIG. 1, the continuous phase feed line 16 is substantially larger than the dispersed phase feed line 18 in order to accommodate the significantly larger volume of continuous phase used. The flow rate of the dispersed and continuous phases can be controlled by pumps and flow regulators, such as the calibrated peristaltic pump and metering needle valve noted above. As shown, the CP and DP can be pumped into the reactor vessel 10 by pumps 24. Alternatively, they can be drawn into the vessel by vacuum or by the pumping action of the mixer, and their flow rates controlled by various flow regulators. Likewise, the continuous phase emulsion can be pumped from the reactor 10 to the solvent evaporation tank 22 by pump 26, in the case of an open reactor system, or by the pumping action of the impeller in a closed system. On a bench scale apparatus, the continuous phase pump 24 can be a simple peristaltic pump. However, due to the pressure head above the dispersed phase, use of a peristaltic pump is difficult for delivering the dispersed phase to the vessel 10. Of course, this problem is reduced or eliminated if a less volatile solvent is used. After forming the emulsion in reactor vessel 10, the continuous phase emulsion is easily drawn or pumped from the reactor vessel 10 into the solvent evaporation tank 22. Of course, depending on the specific apparatus used it may still be necessary to employ pumps in continuous phase and dispersed phase feed lines 16,18 and at the very least flow regulators. Selection of suitable pumps, flow regulators and the like will be well within the skill in the art in view of the instant disclosure.

As noted above, placement of the continuous phase and dispersed phase feed lines 16, 18, can be extremely important, irrespective of whether reaction vessel 10 is open or closed. In particular, it is desirable to have the dispersed phase enter vessel 10 in the optimum zone for formation of microspheres having the desired characteristics.

While not wanting to be bound by theory, an advantage of the present invention is believed to be derived from the use of exceptionally high intensity emulsification. By mechanically mixing the dispersed and continuous phases under high shear forces or high turbulence, the rate of solvent removal from the dispersed phase is believed to be increased. Presumably this is because the increased mixing intensity causes the dispersed phase to interact with more continuous phase per unit time. An increased rate of solvent removal from the dispersed phase to the continuous phase tends to increase the rate of solidification of the dispersed phase. Even in those instances where, due to the polymer, solvents and/or continuous phase used, the dispersed phase inherently solidifies slowly, the increased shear or turbulence induced by the increased mixing intensity associated with the preferred embodiment should provide an enhanced solvent removal effect and hence, an advantageously increased solidification rate and reduced residual solvent content.

High intensity mixing according to the invention is also believed to advantageously effect the size and agent loading of the microspheres. Because of the high shear and/or high turbulence associated with the inventive process, the dispersed phase is forced to form smaller aggregates or droplets. Moreover, fast solidification helps prevent the migration of drug from the dispersed phase, and impedes the ability of the dispersed phase to aggregate into progressively larger droplets. As such, it is possible to obtain very small microspheres having advantageously high drug loading. Assuming the drug is adequately phobic to the continuous phase, such as by the nature of the drug, additives to the CP or the like, or because the drug has enhanced affinity for the polymer or the like, the prompt solidification associated with the high intensity emulsification of the invention can provide very small microspheres having excellent drug loading. The mixing intensity and microsphere sizes associated with the present invention are achieved without serious foaming problems or having to further complicate the process by taking steps to compensate for foaming. Moreover, small microspheres can be achieved even when it is necessary or desirable to employ a more viscous dispersed phase.

Figure 2:
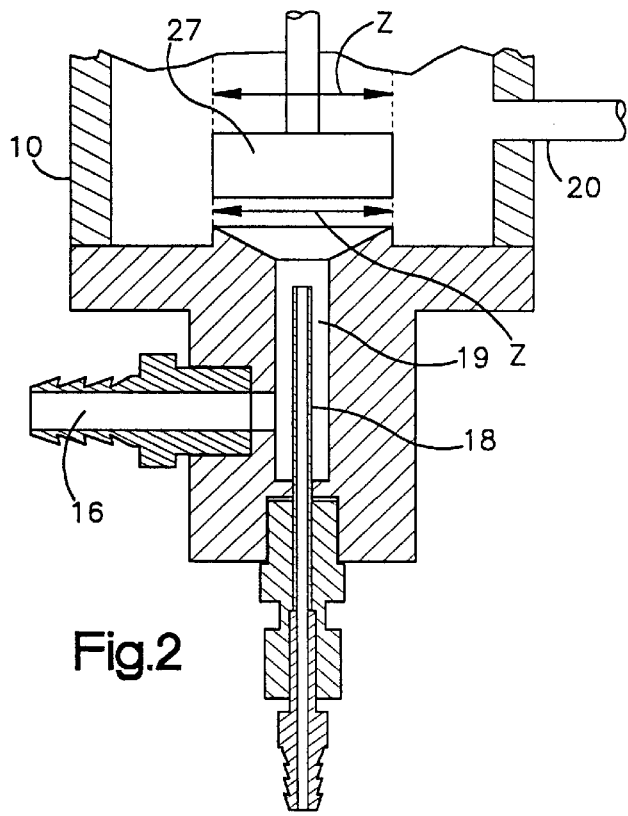
FIG. 2 is a stylized representation of a portion of a preferred reactor vessel according to the invention.

While increased mixing intensity is desirable in accordance with the invention, true shear as between two surfaces, such as an impeller blade and emulsor or stator screen, can also adversely effect the resultant microspheres. For example, where the dispersed phase is introduced directly into a high shear zone, such as the gap between the impeller and screen, the microspheres may solidify so quickly and be subjected to such intense shear forces as to become elongated and misshaped, rather than spherical as is preferred. Accordingly, placement of the feed lines, in particular the dispersed phase feed, can significantly effect the process. By properly locating the introduction of the dispersed phase into the vessel 10, one can ensure the production of uniform spherical particles, and prompt solidification. In the embodiment shown in FIG. 2, the tip of the dispersed phase feed line 18 need not physically enter the vessel chamber. As shown, the feed line can be recessed in channel 19 so that the continuous and dispersed phases can enter the mixing zone together. However, it is desirable that the continuous and dispersed phases not come together too long before entering the reactor vessel.

In accordance with the invention, the disperse phase should be introduced into a highly intense mixing zone, characterized by high shear and/or high turbulence effective to cause a high rate of solvent removal from the dispersed phase to the continuous phase and, preferably, corresponding to a high rate of polymer solidification. However, the dispersed phase should not be introduced into such high shear forces as to misshape or otherwise adversely effect the microspheres. The optimum placement of the feed lines can be determined empirically by those of ordinary skill in the art based on the instant disclosure and will obviously vary depending on the particular apparatus used.

In a preferred embodiment, the high intensity mixing zone is defined as that in which the dispersed phase polymer solidifies within about 20 seconds, more preferably less than about 10 seconds, and still more preferably where it solidifies in less than about 5 seconds. In the preferred LH-RH embodiment, the microspheres are solidified in less than about 3 seconds. Introduction into the suitable mixing zone can be accomplished by locating the dispersed phase input line in close proximity to the emulsification impeller, sonication tip or the like. In a preferred embodiment, shown in FIG. 1, the emulsification apparatus includes an impeller 27, and corresponding stator or emulsor screen 28. The impeller has a diameter defining a diameter of a cylindrical zone extending axially from said impeller and orthoganal the plane of rotation of the impeller, shown in two dimensions at Z in FIG. 1. In this embodiment, the dispersed phase is preferably introduced within the zone Z. More preferably, the dispersed phase is introduced within the zone Z in close proximity, within about 20 mm, of the impeller. Still more preferably, the dispersed phase is introduced about 3 to 10 mm below the impeller. In the case of the preferred Silverson apparatus the impeller has a diameter of 32 mm, and the stator screen a diameter of 34 mm. Thus, in this instance the cylindrical zone will have a diameter of about 32 mm, and wherein the most intense shear forces are set up in the two millimeter gap space between the impeller and stator.

The high turbulence intensity emulsifier may be an impeller type apparatus, a flow restriction device that forces the continuous and dispersed phases through progressively smaller channels causing highly turbulent flow, a high frequency sonication tip or similar apparatus that will be apparent to those of ordinary skill in the art in view of this disclosure. An advantage of non-static mixers is that one can control the mixing intensity independently of the flow rates of the phases into the device. What is important is that it is capable of providing adequate mixing intensity in accordance with the process of the invention. In the case of the preferred impeller type apparatus, suitable emulsification intensity can be obtained by running the impeller in excess of about 5,000 rpm. Preferably, the impeller is run at from about 6,000 to about 10,000 rpm., and most preferably about 7,000. In the case of impeller type devices revolutions per minute provide a good approximation of adequate mixing intensity. Of course, the magnitude of the shear forces, and hence mixing intensity, can also be increased by adjusting the gap space between the impeller and emulsor screen or stator. Likewise, the intensity experienced by the dispersed phase can also be adjusted by properly locating the feed as discussed above. Commercially available apparatus adaptable to the instant process include in-line mixers from Silverson, Ross mixers and the like. A significant advantage of the preferred embodiment is that high intensity emulsification, such as that induced using an impeller at speeds in excess of 5,000 rpm's, can be employed without creating a foaming problem.

Notably, depending on the active agent, polymer, solvents, continuous phase, the volume of each, and numerous other factors, some systems simply will not solidify rapidly, even when the intensity of mixing is substantial. In such systems, the most significant advantages of the inventive process, for example, scale up, elimination the foaming problem and associated ability to obtain small particles with good agent loading, product uniformity and the like, are not lost.

Once the emulsion of dispersed phase and continuous phase is formed, the emulsion is continuously transferred from the reaction vessel 10 to a solvent removal tank 22. As used herein, transferring the 'emulsion' may be an actual emulsion, but in the preferred embodiment will be more accurately a suspension of solidified dispersed phase particles suspended in the continuous phase. If solidification is not especially fast, the emulsion being transferred may consist of suspension of dispersed phase droplets in the process of solidifying.

In the case of an open reaction vessel the transfer is done with one or more pumps. In the case of the preferred closed reaction vessel the transfer can be done by using the mixer itself as a pump, or since the solvent evaporation tank can draw a vacuum, it can be done by vacuum. Solvent removal is important in the preparation of microspheres, especially when the resulting microspheres are intended for clinical applications.

Interestingly, it is observed that in the preferred system, even though solidification of microspheres is virtually instantaneous, the formed microspheres are nevertheless susceptible to give up additional residual solvent into the continuous phase. Accordingly, it is believed that some form of solvent evaporation process is necessary to obtain the desirably low residual solvent contents necessary for many clinical applications.

In the solvent evaporation tank the composition is stirred. Any vessel in which the atmosphere can be controlled could suffice. Typically, the composition will be stirred in the solvent evaporation tank for 3 to 8 hours, and in the preferred embodiment about 4. Head space is preferred to be about ⅓rd the tank capacity. Changing the air in the head space of the vessel e.g., by replacing the air with new air, nitrogen or other inert gas, has proven to be a highly effective means of maximizing solvent removal. In the preferred embodiment the flow rate is about 30 L/min with a 25 liter head space. In this embodiment, the air in the head space is changed about once times a minute. Other solvent removal steps suitable for use in connection with the present invention would be apparent to those of ordinary skill in the art in view of the instant disclosure. Thus, increased or infinite dilution with continuous phase, or replacing solvent saturated continuous phase with fresh continuous phase, the use of an air sweep and/or vacuum and the like can be used to extract additional solvent in the solvent removal tank after formation of the microspheres. Infinite dilution is not typically convenient for production level manufacturing. However, for some products, such as those sensitive to temperature, it may be useful.

While not wanting to be bound by theory, it is believed that in the preferred embodiment wherein the active agent is LH-RH and the polymer is a hydrophilic d,l-poly(lactide-co-glycolide), solvent removal by evaporation, which preferably includes an air sweep, is necessary to obtain the desired degree of solvent removal.

Drug load, in the case of the preferred LH-RH microspheres, is targeted at 20.5% based on the total solid. In practice, drug loads on the order of 15 to 19% can be obtained. Of course, the nature of the drug, the desired release profile, the nature of the polymer and, of course, processing can all effect the desired and actual drug load. In the typical case, drug loads on the order of 5% to 20% based on the combined weight of drug and polymer are desired and achievable with the process of the invention.

Advantageously, once the desired drug load is obtained, and the parameters of feed rate, temperature etc. are determined, scaling up to larger batches, including production level batches, becomes a simple matter of running the process longer. No additional feed tubes, emulsifiers, impellers or the like are necessary to produce a larger number of microspheres having the desired characteristics. Moreover, the microspheres produced during the continuous process of the invention are exceptionally uniform in terms of size, agent load and the like, regardless of when during the process they were produced.

These and other aspects of the invention will be further understood from the following non-limiting examples.

Unless otherwise noted the following apparatus was used in the examples. The Silverson in-line mixer was modified with the additional inlet for the dispersed phase as hereinbefore described, and connected to a Silverson stirrer model 4LR. The outlet tube was connected to a 7 liter jacketed bio-reactor from Applikon. One of the top plate ports of the Applikon was connected to the vacuum pump, another to a dry 0.2 µm filter to serve as the air inlet, another served as the inlet from the Silverson, and the fourth served as the harvest line.

EXAMPLE 1

This is an example of a typical procedure used to prepare microspheres of poly(lactide-co-glycolide) and Leuprolide (LH-RH).

The hydrophilic polymer RG503H is a 50:50 copolymer of poly(lactide-co-glycolide) from Boehringer Ingelheim having an inherent viscosity of 0.42 dL/g. This polymer has a weight average molecular weight ($M_W$) on the order of 30,000. A solution of this polymer was prepared by dissolving 7.0 grams RG503H in 36 g dichloromethane. The drug solution was prepared separately by dissolving 1.00 g leuprolide acetate in 8.56 g methanol. The dispersed phase (DP) was prepared by combining the leuprolide solution and the polymer solution with mixing. The DP thus formed is a homogeneous light yellow, relatively clear solution. The DP was then transferred into a 124 mL pressure addition funnel and connected to the DP inlet to of the Silverson unit through a micrometer teflon needle valve. Head pressure was applied to the addition funnel (10 psi) above the continuous phase (CP). The stop-cock of the addition funnel was kept closed until the DP addition started.

The continuous phase (CP) was 0.35% polyvinyl alcohol (PVA) solution (w/v) prepared in a 7 liter beaker by dissolving 14.0 g PVA (cold water soluble, MW 30,000–70,000) in 4000 mL water. The CP addition tube to the Silverson unit from the CP tank used a peristaltic pump for flow control. The outlet tube of the Silverson unit was connected to the solvent evaporation tank, which is a 7 liter Applikon reactor with a jacketed vessel and lip-seal stirrer assembly.

The Silverson unit was primed with CP and trapped air in the cell was removed by opening the bleed valve. The stirrer motor of the Silverson was turned on to 7000 rpm and the CP and the DP were introduced into the reactor simultaneously. The required flow rate of CP and DP were achieved and maintained constant using the peristaltic pump (for CP) and needle valve (for DP). The addition time was 2 minutes, during which 52.6 grams of DP and 4000 mL of CP were introduced to the mixer at a constant rate of flow.

The microspheres were formed in the Silverson unit and delivered as a suspension into the solvent evaporation tank. The head space air was constantly replaced using the vacuum pump. The air flow through the head space was approximately 29 standard liters per minute. The temperature of the evaporation tank was increased from 25° to 42° C. and maintained for 3 hours. The higher temperature and air sweep helped the system to achieve lower residual solvent in the microspheres.

After solvent evaporation, the system temperature was lowered to 25° C. and the microspheres harvested by pressure filtration (5–20 psi) onto a 5 µm filter using a 2000 mL stirred cell assembly (M-2000 from Amicon). The microspheres were washed with 2000 mL WFI and freeze dried in bulk as a concentrated suspension in WFI (approx. 0.3 g/mL). Of course, this procedure will change upon scale up to commercial production.

The microspheres prepared according to this example had 9.88% drug load showing 79% drug incorporation efficiency. Microscope analysis showed that the microspheres were spherical and the particles ranged from non-porous to partially porous. Small particles were non-porous while larger particles showed some porosity. The bulk density of the microspheres was 0.588 g/cc. The particle size distribution analysis showed that 50% of the particles were below 18 µm (volume distribution), and 80% of the particles were between 7 and 36 µm. The residual solvent (methylene chloride or methanol) was undetectable (i.e., less than about 20 ppm).

EXAMPLE 2

As illustrated by this example, a significant advantage of the preferred continuous flow process according to the invention is the product consistency during processing. Prior processes are unable to produce microspheres having virtually identical characteristics at the end of the production run as the ones produced at the beginning and middle of the run. This is a significant commercial advantage.

The microspheres were prepared in the same manner as in Example 1, using 25% excess DP and CP. The DP contained 8.75 g RG503H, 1.25 g Leuprolide acetate, 45 g methylene chloride and 10.7 g methanol. The CP was 5000 mL 0.35% PVA. In this example, the microsphere suspension produced in the Silverson reactor was not transferred to the solvent removal tank. Instead, each 1000 mL fraction (the collection time for each fraction being approx. 24 seconds) were collected in a 2000 mL beaker. Thus, five fractions of equal volume was collected. The microspheres from each fraction were separated by filtration, freeze dried in bulk and compared.

Microscopic analysis showed that the morphology of the microspheres obtained in all five fractions was identical. Larger particles showed some porosity while the smaller particles were non-porous. The following Table I shows that each fraction (Frxn) of microspheres produced throughout the process have excellent consistency.

TABLE I

|  | Frxn 1 | Frxn 2 | Frxn 3 | Frxn 4 | Frxn 5 |
| --- | --- | --- | --- | --- | --- |
| Load | 11.17 | 11.31 | 10.96 | 11.05 | 10.99 |
| Size (µm) | | | | | |
| 10% under | 9.6 | 8.9 | 8.9 | 9.3 | 8.9 |
| 50% under | 18.1 | 17.4 | 17.8 | 17.8 | 17.4 |
| 90% under | 33.3 | 32.6 | 35.5 | 34.4 | 32.6 |
| Blk Dens. | 0.40 | 0.48 | 0.48 | 0.47 | 0.48 |

The residual methylene chloride values were higher in all the fractions (approx. 8000 ppm) because no solvent evaporation was performed on the microspheres.

EXAMPLE 3

In this example, a hydrophobic polymer was used. Boehringer Ingelheim RG502 is a 50:50 co-polymer of PLGA with an inherent viscosity of 0.2 dl/g. The preparation procedure was similar to Example 1, except for the composition of the DP. Here, a polymer solution was prepared by dissolving 8.77 g RG502 in 20 g dichloromethane. The drug solution was separately prepared by dissolving 1.25 g leuprolide in 4 g methanol. The polymer and drug solutions were mixed to form the DP. Thereafter, 5000 mL of CP was added by adjusting the micrometer needle valve setting for the DP addition so that the time for both DP and CP addition was approximately the same (2 minutes). Silverson stirring, solvent evaporation and microsphere harvesting were all performed as in Example 1.

The drug incorporation efficiency of the resulting microspheres was 65% and the microspheres had a drug load of 8.17% Microscope analysis showed that the microspheres had spherical geometry and were porous. The bulk density of the microspheres was 0.23. The particle size distribution analysis showed that 50% of the particles were below 25.6 µm (volume distribution), 80% of the particles were between 12.2 and 44.0 µm. The residual methylene chloride and methanol in the microspheres was undetectable (less than 20 ppm).

EXAMPLE 4

In this example, a homopolymer of polylactic acid was used. 8.75 g polylactic acid (R202H from Boeringer Ingelheim) having an inherent viscosity of 0.18 dL/g was dissolved in 20 g dichloromethane. Drug solution was prepared by dissolving 1.25 g leuprolide in 4 g methanol. The polymer and the drug solutions were mixed to form the DP, which appeared as a homogeneous, nearly colorless solution. The microspheres were prepared and harvested as disclosed in Example 1 using 5000 mL of continuous phase.

These microspheres had a drug incorporation efficiency of 85% and a drug load of 10.58%. Microscope analysis showed that the microspheres had perfect spherical geometry, with most of the spheres appearing non-porous. A few of the larger particles appeared to have pores at the center of the core. The bulk density of the microspheres was 0.615 g/mL. The particle size analysis showed that 50% of the particles were below 16.0 µm (volume distribution), and 80% of the particles were between 5.8 and 30.2 µm. The microspheres contained 79 ppm methylene chloride and an undetectable amount (less than 10 ppm) of methanol.

EXAMPLE 5

In this example, the microspheres were prepared as in Example 1 using 8.75 g RG503H, 1.25 g leuprolide, 45 g methylene chloride and 10.7 g methanol for the DP. The stirring speed was increased to 9000 rpm, using 5000 mL CP of 0.35% PVA solution. The drug incorporation efficiency was 70.7% and the drug load was 8.84% in the microspheres. Microscope analysis showed that the microspheres were smaller, had a spherical geometry, and were predominantly non-porous. The bulk density of the microspheres was 0.510 g/mL. The particle size distribution analysis showed that 50% of the particles fall below 15.5 µm (volume distribution) and 80% of the particles were between 8.1 and 24.8 µm. The microspheres contained 47 ppm residual methylene chloride and an undetectable amount of methanol (less than 10 ppm).

EXAMPLE 6

In this example, microspheres were prepared containing a proteinaceous agent. The active agent was the protein Human Serum Albumin. The microspheres were prepared by forming a w/o/w emulsion using RG503H polymer. The preparation procedure was the same as in Example 1 except that the dispersed phase was formed by preparing a polymer solution of 8.75 g polymer in 45 g methylene chloride. 5 mL of 25% w/v solution of human serum albumin was added slowly into polymer solution while stirring using a magnetic stirrer. The dispersed phase thus obtained was stirred vigorously for about 5 minutes to form a milky white fine suspension. The microspheres were prepared as in Example 1 except that the stirring speed of the Silverson unit was 6000 rpm. The microspheres were harvested and freeze dried as in Example 1.

Microscope analysis showed that the microspheres had perfectly spherical geometry and were highly porous. The bulk density of the microspheres was 0.03 g/mL. The particle size distribution analysis showed that 50% of the particles were below 48.4 μm, and 80% were between 23.0 and 69.7 μm. The microspheres did not have any detectible residual methylene chloride.

EXAMPLE 7

In this example, microspheres were prepared from RG503H and a non-peptide drug. The polymer solution was prepared by dissolving 8.74 g RG503H in 45 g dichloromethane. 1.25 g dipyridamole was added slowly to the polymer solution and 2.53 g methanol was added to make the homogeneous solution, which appeared bright yellow. 5000 mL of 0.35% PVA solution was used as the continuous phase. The microspheres were prepared, harvested and freeze dried as in Example 1.

These microspheres had an 88% drug incorporation efficiency with an 11.0% drug load. Microscope analysis showed that the microspheres were spherical, generally smaller and predominantly non-porous. The bulk density of the microspheres was 0.45 g/mL. The particle size distribution analysis showed that 50% of the particles were below 13.5 μm (volume distribution), and 80% of the particles were between 5.8 and 20.0 μm. The microspheres had 107 ppm residual methylene chloride and undetectable methanol.

Many modifications and variations of the invention will be apparent to those skilled in the art in light of the forgoing detailed disclosure. Therefore, within the scope of the appended claims, the invention can be practiced otherwise than as specifically shown and described.

What is claimed is:

1. A continuous method of making active agent containing polymer bodies comprising:
   a) forming a dispersed phase comprising active agent and polymer;
   b) providing a continuous phase in which said dispersed phase will form an emulsion;
   c) continuously introducing dispersed phase into a reactor vessel at a dispersed phase feed rate, and continuous phase into said reactor vessel at a continuous phase feed rate, said reactor vessel including means for forming an emulsion, and forming an emulsion of said dispersed phase in said continuous phase;
   d) continuously transporting said emulsion from said reactor vessel to a solvent removal vessel to remove solvent.

2. The method of claim 1 wherein said dispersed phase is fed to said reaction vessel at a rate of from about 4 ml/min to about 400 ml/min, and said continuous phase is fed to said reactor vessel at a rate of from about 1000 ml/min. to about 20,000 ml/min.

3. The method according to claim 1 wherein said dispersed phase includes a hydrophilic peptide active agent and a copolymer of lactide and glycolide, and comprising emulsifying said dispersed and continuous phases in a manner effective to provide an average particle size of from about 5 μm to about 40 μm, and an active agent load of at least about 9%.

4. The method according to claim 1 wherein said dispersed phase includes a hydrophilic peptide active agent and a copolymer of lactide and glycolide, and comprising emulsifying said dispersed and continuous phases in a manner effective to provide an average particle size of from about 5 μm to about 40 μm, and an active agent load of at least about 15%.

5. The method of claim 1 wherein said continuous phase and dispersed phase are introduced into said reactor in a ratio of from 5:1 to 500:1.

6. The method of claim 1 wherein said continuous phase and dispersed phase are introduced into said reactor in a ratio of from 40:1 to 200:1.

7. The method of claim 1 wherein said means for forming an emulsion comprises an impeller.

8. The method of claim 1 wherein said means for forming an emulsion comprises an impeller and said mixing is performed by running said impeller in excess of about 5,000 revolutions per minute.

9. The method of claim 1 wherein said means for forming an emulsion comprises an impeller, said impeller having a diameter defining a diameter of a cylindrical zone extending axially from said impeller, and wherein said dispersed phase is introduced into said axially extending zone.

10. The method of claim 1 wherein said means for forming an emulsion produces a mixing zone effective to cause solidification of dispersed phase polymer within about 10 seconds, and said dispersed phase is introduced into said reaction vessel in said mixing zone.

11. The method of claim 1 wherein said dispersed phase is a homogeneous solution.

12. The method of claim 1 wherein said dispersed phase is an emulsion.

13. The method according to claim 1 wherein the average residence time of said dispersed phase in said reactor is less than about 5 seconds.

14. The method of claim 1 comprising emulsifying said dispersed and continuous phases in a manner adapted to cause solidification of said dispersed phase polymer within about 10 seconds.

15. The method of claim 1 comprising emulsifying said dispersed and continuous phases in a manner adapted to cause solidification of said dispersed phase polymer within about 5 seconds.

16. The method of claim 1 wherein said means for forming an emulsion comprises an impeller and said step of forming said emulsion comprises running said impeller in excess of from about 6,000 to about 10,000 revolutions per minute.

17. The method according to claim 1 wherein said method steps are carried out for a period sufficient to produce a desired population of microspheres, and wherein microspheres produced at the beginning of said period have substantially the same size and agent load as microspheres produced at the end of said period.

18. A microsphere made by the method of claim 1.

19. A microsphere made by the method of claim 3.

20. A microsphere made by the method of claim 14.

21. The method of claim 1 comprising providing an aqueous continuous phase.

22. The method of claim 1 comprising carrying out said steps for a period sufficient to produce a desired population of polymer bodies, and wherein said polymer bodies produced at the beginning of said period have substantially the same size distribution as the polymer bodies produced at the end of said period.

23. The method of claim 1 comprising carrying out said steps for a period sufficient to produce a desired population of polymer bodies, and wherein said polymer bodies produced at the beginning of said period have substantially the same agent load as the polymer bodies produced at the end of said period.

24. The method of claim 1 comprising providing an aqueous continuous phase, and forming said dispersed phase to include LHRH or an analog thereof and a copolymer of lactide and glycolide, and wherein solidification of said dispersed phase commences within about 10 seconds.

25. The method of claim 1 wherein said continuous phase and dispersed phase feed rates are controlled independently of said means of forming said emulsion.

26. The method of claim 1 wherein said means of forming said emulsion comprises an in-line mixer, and a mixing intensity for forming said emulsion is controlled independently of said continuous phase and dispersed phase feed rates.

* * * * *